(12) United States Patent
Suzuki et al.

(10) Patent No.: US 12,281,977 B2
(45) Date of Patent: Apr. 22, 2025

(54) GAS MEASUREMENT DEVICE HAVING VARIABLE VOLUME

(71) Applicants: SINTOKOGIO, LTD., Nagoya (JP); National University Corporation TOYOHASHI UNIVERSITY OF TECHNOLOGY, Toyohashi (JP)

(72) Inventors: Yoshihisa Suzuki, Toyokawa (JP); Toshihiko Noda, Toyohashi (JP); Kazuaki Sawada, Toyohashi (JP)

(73) Assignees: SINTOKOGIO, LTD., Nagoya (JP); National University Corporation TOYOHASHI UNIVERSITY OF TECHNOLOGY, Toyohashi (JP)

( * ) Notice: Subject to any disclaimer, the term of this patent is extended or adjusted under 35 U.S.C. 154(b) by 237 days.

(21) Appl. No.: 17/802,306

(22) PCT Filed: Feb. 3, 2021

(86) PCT No.: PCT/JP2021/003915
§ 371 (c)(1),
(2) Date: Aug. 25, 2022

(87) PCT Pub. No.: WO2021/176931
PCT Pub. Date: Sep. 10, 2021

(65) Prior Publication Data
US 2023/0091525 A1    Mar. 23, 2023

(30) Foreign Application Priority Data
Mar. 5, 2020  (JP) .................... 2020-038068

(51) Int. Cl.
*G01N 1/22* (2006.01)
*G01N 15/10* (2006.01)

(52) U.S. Cl.
CPC .. *G01N 15/1023* (2024.01); *G01N 2015/1028* (2024.01); *G01N 2015/1029* (2024.01)

(58) Field of Classification Search
CPC .......... G01N 33/0014; G01N 33/0016; G01N 25/4886; G01N 25/4873; G01N 25/48;
(Continued)

(56) References Cited

U.S. PATENT DOCUMENTS

| | | | |
|---|---|---|---|
| 5,395,503 A * | 3/1995 | Parce .................. | G01N 27/327 204/415 |
| 7,608,984 B2 * | 10/2009 | Wright ................. | F04B 45/047 310/329 |

(Continued)

FOREIGN PATENT DOCUMENTS

| | | |
|---|---|---|
| CN | 206378484 U | 8/2017 |
| JP | 2001-264222 A | 9/2001 |

(Continued)

OTHER PUBLICATIONS

International Preliminary Report on Patentability mailed Sep. 15, 2022 for PCT/JP2021/003915.
(Continued)

*Primary Examiner* — Tran M. Tran
(74) *Attorney, Agent, or Firm* — Faegre Drinker Biddle & Reath LLP

(57) ABSTRACT

The gas measurement device includes a gas sensor disposed in a gas chamber, a filter configured to control passing gas molecules to the gas chamber, and a driving unit configured to move at least a part of a member defining the gas chamber.

7 Claims, 5 Drawing Sheets

(58) Field of Classification Search
CPC ......... G01N 2030/32; G01N 2030/326; G01N 2001/14; G01N 2001/2288; G01N 2001/2276; G01N 1/2205; G01N 1/2247; G01N 1/24; G01N 1/26; G01N 1/2273; B01L 2400/048; B01L 2400/047; F04B 45/00

See application file for complete search history.

(56) References Cited

U.S. PATENT DOCUMENTS

| | | | | |
|---|---|---|---|---|
| 9,097,244 B2 * | 8/2015 | Matsuzaki | ............ | F04B 17/03 |
| 9,518,970 B2 * | 12/2016 | Burgi | ............ | G01N 33/0016 |
| 9,808,567 B2 * | 11/2017 | O'Mahony | ............ | G01L 19/144 |
| 10,101,291 B2 * | 10/2018 | Ho | ............ | G01N 33/0036 |
| 10,156,553 B2 * | 12/2018 | Choi | ............ | G01N 33/0009 |
| 10,206,021 B2 * | 2/2019 | Lahti | ............ | H04R 1/028 |
| 10,495,669 B2 * | 12/2019 | Lem | ............ | A61B 5/28 |
| 10,569,076 B2 * | 2/2020 | Kurihara | ............ | F16K 17/164 |
| 10,677,773 B2 * | 6/2020 | Mou | ............ | G01N 33/007 |
| 10,678,298 B2 * | 6/2020 | Mou | ............ | H04R 1/025 |
| 10,688,225 B2 * | 6/2020 | Takeuchi | ............ | A61M 1/65 |
| 10,845,274 B2 * | 11/2020 | Richter | ............ | F04B 53/20 |
| 10,914,299 B2 * | 2/2021 | Hannemann | ............ | F04B 43/02 |
| 10,928,345 B2 * | 2/2021 | Brown | ............ | G01N 33/0039 |
| 11,002,719 B2 * | 5/2021 | Mou | ............ | G01N 29/222 |
| 11,067,073 B2 * | 7/2021 | Chen | ............ | F04B 43/046 |
| 11,162,487 B2 * | 11/2021 | Mou | ............ | F04B 53/20 |
| 11,187,215 B2 * | 11/2021 | Mou | ............ | G08B 21/12 |
| 11,187,655 B2 * | 11/2021 | Ryu | ............ | G01N 21/3504 |
| 11,204,335 B2 * | 12/2021 | Mou | ............ | G01N 33/0047 |
| 11,255,322 B2 * | 2/2022 | Mou | ............ | H04M 1/035 |
| 11,391,708 B2 * | 7/2022 | Mou | ............ | B01L 3/502715 |
| 11,415,491 B2 * | 8/2022 | Yang | ............ | F04B 45/047 |
| 11,680,957 B2 * | 6/2023 | Govyadinov | ............ | G01F 15/00 73/861.05 |
| 11,860,175 B2 * | 1/2024 | Scheffler | ............ | G01N 35/00693 |
| 11,892,429 B2 * | 2/2024 | Hutter | ............ | G01N 1/24 |
| 11,921,021 B2 * | 3/2024 | Hamasaki | ............ | G01N 33/0016 |
| 11,939,970 B2 * | 3/2024 | Okaguchi | ............ | F04B 41/06 |
| 2009/0232683 A1 * | 9/2009 | Hirata | ............ | F04B 45/047 417/413.2 |
| 2012/0034109 A1 * | 2/2012 | Tout | ............ | F04B 43/046 417/313 |
| 2013/0209278 A1 | 8/2013 | Locke et al. | | |
| 2014/0134053 A1 * | 5/2014 | Mayer | ............ | G01N 33/0009 422/83 |
| 2015/0369781 A1 * | 12/2015 | Zheng | ............ | G01N 30/32 422/503 |
| 2016/0187214 A1 | 6/2016 | Al-Hemyari | | |
| 2016/0271305 A1 * | 9/2016 | Kurihara | ............ | A61M 1/73 |
| 2019/0257803 A1 * | 8/2019 | Brown | ............ | G01N 33/0031 |
| 2023/0204552 A1 * | 6/2023 | Decker | ............ | G01N 33/0016 73/23.2 |
| 2024/0027412 A1 * | 1/2024 | Schaller | ............ | G01N 33/0016 |

FOREIGN PATENT DOCUMENTS

| | | |
|---|---|---|
| JP | 2003-028764 A | 1/2003 |
| JP | 2009-271059 A | 11/2009 |
| JP | 2015-516529 A | 6/2015 |
| JP | 2016-090460 A | 5/2016 |
| WO | WO-2013/119854 A2 | 8/2013 |
| WO | WO-2017/207594 A1 | 12/2017 |

OTHER PUBLICATIONS

Extended European Search Report issued Jan. 30, 2024 in Application No. 21763815.4.

* cited by examiner (A)

(B)

(A)

(B)

(A)

(B)

GAS MEASUREMENT DEVICE HAVING VARIABLE VOLUME

TECHNICAL FIELD

The present disclosure relates to a gas measurement device.

BACKGROUND ART

Patent Document 1 discloses a gas measurement device in which external air is sucked by a fan. The gas measurement device includes a casing and a sensor inside the casing. The casing is provided with a gas flow hole communicating between the inside and the outside of the casing. Inside the casing, a fan is attached at a position facing the gas flow hole. The sensor inside the casing detects the gas concentration of the outside air sucked by the operation of the fan.

CITATION LIST

Patent Document

Patent Document 1: Japanese Unexamined Patent Publication No. 2009-271059

In the gas measurement device described in Patent Document 1, a fan is required to suck gas. The present disclosure provides a gas measurement device capable of measuring gas with a simple configuration.

Solution to Problem

A gas measurement device according to one aspect of the present disclosure includes a gas sensor disposed in a gas chamber, a filter configured to control passing gas molecules to the gas chamber, and a driving unit configured to move at least a part of a member that defining the gas chamber.

In this gas measurement device, at least the part of the member defining the gas chamber is moved by the driving unit. Accordingly, the volume of the gas chamber increases or decreases. When at least the part of the member defining the gas chamber moves such that the volume of the gas chamber increases, the pressure in the gas chamber decreases from outside the gas chamber. External gas is drawn into the gas chamber through a filter that controls gas molecules. When at least the part of the member defining the gas chamber moves such that the volume of the gas chamber decreases, the pressure in the gas chamber increases from outside the gas chamber. The gas in the gas chamber is exhausted to the outside of the gas chamber. Therefore, the gas measurement device can measure gas with a simpler structure than a gas measurement device including a fan.

In one embodiment, the member defining the gas chamber includes an upper portion, a bottom portion, a side wall, and a movable portion that is moved by the driving unit. The upper portion defines a top surface of the gas chamber and includes the filter. The bottom portion defines a bottom surface of the gas chamber and the gas sensor is disposed therein. The sidewall defines a side of the gas chamber and is sandwiched between the upper portion and the bottom portion. The movable portion defines a side surface of the gas chamber together with the side wall, and is connected to the upper portion, the bottom portion, and the side wall. At least the part of the member defining the gas chamber is a movable portion that is moved by the driving unit. The driving unit may move the movable portion along the top surface, the bottom surface, and the side wall. The volume of the gas chamber defined by the movable portion is increased or decreased by the movement of the movable portion. In this case, the gas measurement device can suck gas by the moving movable portion.

In one embodiment, the movable portion may be in close contact with the gas sensor and the filter. The driving unit may move the movable portion along the gas sensor and the filter. In this case, the gas measurement device is downsized compared to a gas measurement device in which the movable portion is not in close contact with the filter and the gas sensor.

In one embodiment, the member defining the gas chamber may include an upper container, a lower container, and a driving unit. The upper container is provided with a filter and an opening at the lower end. In the lower container, a gas sensor is disposed and an opening is provided at an upper end. The driving unit is held between the lower container and the upper container. At least the part of the member defining the gas chamber, which is moved by the driving unit, is an upper container. The driving unit may move the upper container in the up-down direction with respect to the lower container. In this configuration, the gas flow through the filter is perpendicular to the gas sensor. Therefore, the gas measurement device can stabilize the gas flow to be sucked.

In one embodiment, the member defining the gas chamber may include a container and an elastic member. The container is provided with an opening in which a filter and a gas sensor are disposed. The elastic member is a film-like member fixed to the container so as to close the opening. At least the part of the member defining the gas chamber, which is moved by the driving unit, is the elastic member. The driving unit may move the elastic member so that the gas chamber protrudes. In this case, compared to a gas measurement device in which an elastic member is not included in a member that defines the gas chamber, the gas measurement device can intake gas with a simple structure.

In one embodiment, the member defining the gas chamber may include a valve that is opened when the pressure in the gas chamber is higher than the external pressure and is closed when the pressure in the gas chamber is lower than the external pressure. In this case, the gas measurement device can exhaust in which a valve is not included in a member that defines the gas chamber, the gas measurement device can exhaust gas in the gas chamber at high speed.

Advantageous Effects of Invention

According to the gas measurement device of the present disclosure, gas can be measured with a simple configuration.

Figure 5:
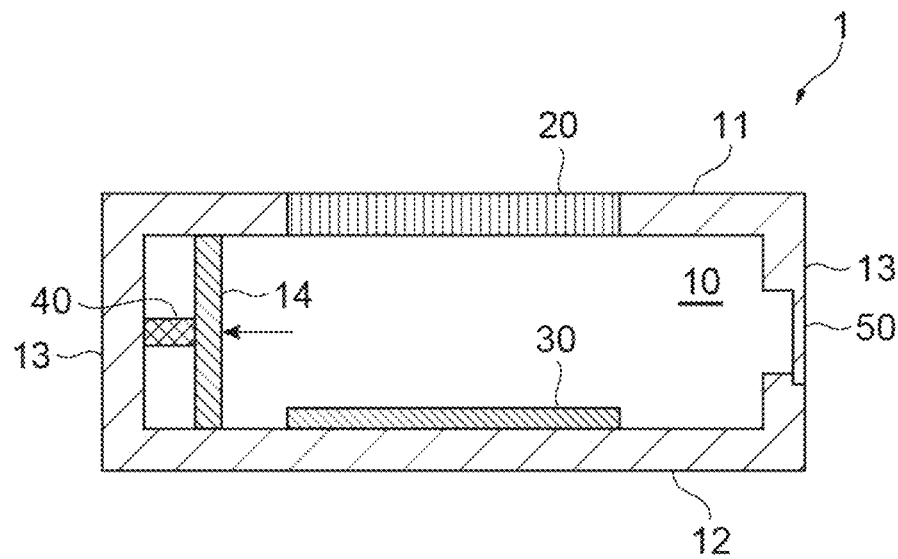
Figure 5:
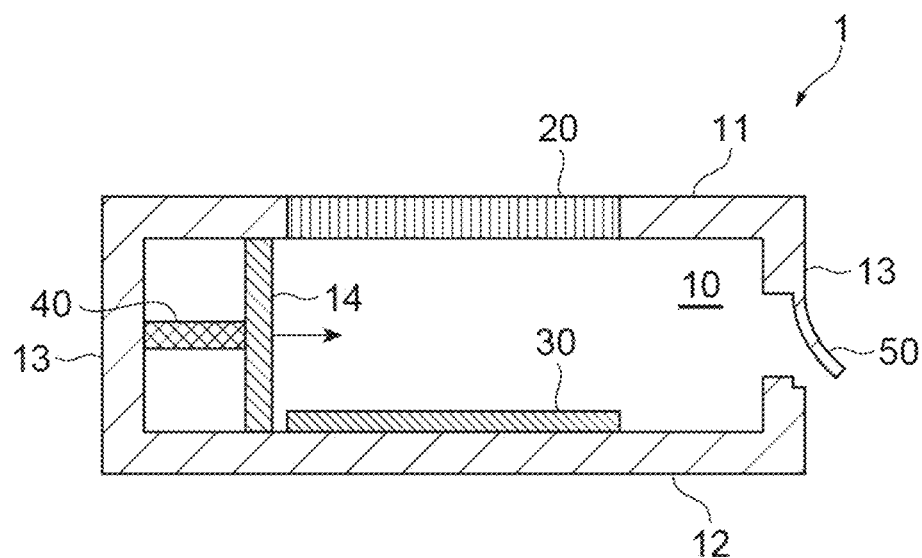

of FIG. 5 (A) is a cross-sectional view showing an example of a gas measurement device in which a valve is closed. (B) of FIG. 5 is a cross-sectional view showing an example of the gas measurement device in which the valve is opened.

DESCRIPTION OF EMBODIMENTS

An embodiment of the present disclosure is described below with reference to the drawings. In the description below, the same or equivalent elements are denoted by the same reference characters, and overlapping description is not repeated. Dimension ratios of the drawings do not necessarily match with those described. Terms "up", "down", "left", and "right" are based on the illustrated states and are for convenience.

Figure 1:
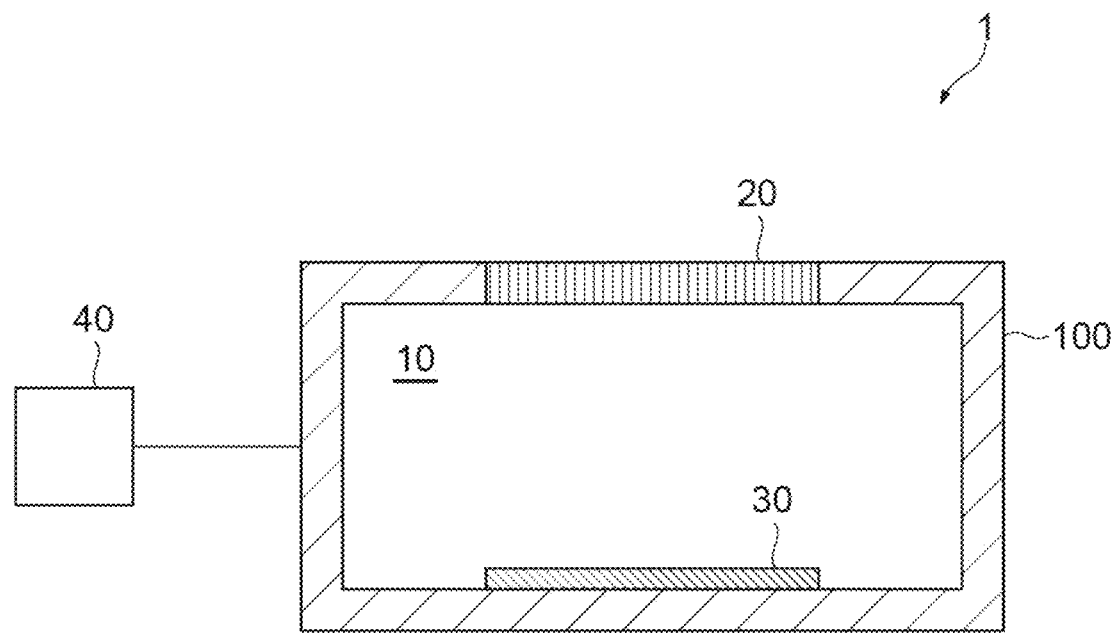
FIG. 1 is a cross-sectional view illustrating an example of a gas measurement device according to an embodiment.

[Configuration of Gas Measurement Device] FIG. 1 is a cross-sectional view illustrating an example of a gas measurement device 1 according to an embodiment. The gas measurement device 1 shown in FIG. 1 is a device for measuring gas components. The gas measurement device 1 may be provided as an electric circuit component. As an example, the gas measurement device 1 is a micro electro mechanical systems (MEMS) device. The gas measurement device 1 includes a member 100 defining a gas chamber, a filter 20, a gas sensor 30, and a driving unit 40.

The filter 20 controls gas molecules passing through the filter 20. The control refers to, for example, sieving gas molecules passing through the filter 20 based on their sizes. As an example, the filter 20 is a MEMS device having a plurality of openings through which gas molecules pass.

The filter 20 controls the size of gas molecules passing through the filter 20 by varying the size of the plurality of openings.

The control may be to change the traveling direction of gas molecules passing through the filter 20 by electrostatic force. As an example, the filter 20 is a MEMS device having a plurality of electrodes through which gas molecules pass. The filter 20 controls the traveling direction of ionized gas molecules passing through the filter 20 by changing the voltage applied to the plurality of electrodes.

The control may be to cause the mixed gas passing through the filter 20 to react by a catalyst. The gas species contained in the mixed gas changes to another gas species by a reaction in response to the temperature of the catalyst. As an example, the filter 20 is a MEMS device having a catalyst with which gas molecules come into contact. The filter 20 controls the gas species contained in the mixed gas passing through the filter 20 by changing the temperature of the catalyst.

The filter 20 is in any case fluid-resistance to the gas. The term "fluid resistance" refers to a resistance that acts to impede the flow of gas through filter 20. Therefore, in order to replace the gas molecules in the gas chamber 10 with the external gas molecules, a predetermined time corresponding to the fluid resistance is required.

The gas sensor 30 is disposed in the gas chamber 10. The gas sensor 30 is an element that outputs an electric signal in response to the concentration of a predetermined gas species. As an example, the gas sensor 30 is a semiconductor type sensor that detects gas molecules attached to the surface. The gas chamber 10 is defined by a gas-impermeable member 100. Therefore, the gas sensor 30 provided in the gas chamber 10 detects the gas molecules controlled by the filter 20.

The driving unit 40 moves at least a part of the member 100 defining the gas chamber 10. The driving unit 40 moves at least the part of the member 100 so as to vary the volume of the gas chamber 10. As a more specific example, the driving unit 40 moves at least the part of the member 100 so that the shape of the gas chamber 10 changes. The movement may be reciprocating. The driving unit 40 may move the entire member 100. This case is also included in moving at least the part of the member 100 that defines the gas chamber 10. The driving unit 40 may be a piezo pump. Alternatively, a piezoelectric actuator and a MEMS actuator may be used. The driving unit 40 is connected to a power source (not shown). Details of the driving unit 40 will be described later.

The member 100 defining the gas chamber is formed of a material impermeable to gas. The member 100 may be constituted by a plurality of members. The member 100 may include the filter 20 and the gas sensor 30. Details of the member 100 will be described later.

According to the gas measurement device 1 configured as described above, a part of the member 100 that defines the gas chamber 10 is moved by the driving unit 40. As a result, the volume of the gas chamber 10 increases or decreases. When at least the part of the member 100 moves so that the volume of the gas chamber 10 increases, the pressure of the gas chamber 10 decreases from the outside of the gas chamber 10. External gas is sucked into the gas chamber 10 through a filter 20 for controlling gas molecules. When at least the part of the member 100 moves so that the volume of the gas chamber 10 decreases, the pressure of the gas chamber 10 increases from the outside of the gas chamber 10. The gas in the gas chamber 10 is exhausted to the outside of the gas chamber 10. Therefore, the gas measurement device 1 can suck gas with a simple structure compared to a gas measurement device including a fan.

Figure 2:
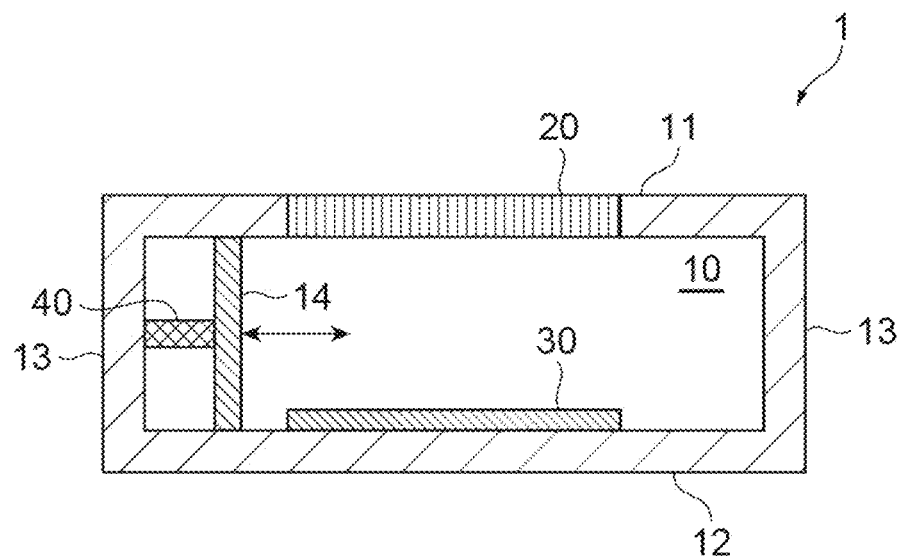
FIG. 2 (A) is a cross-sectional view showing an example of a gas measurement device including a movable portion in a member defining a gas chamber. (B) of FIG. 2 is a cross-sectional view showing an example of the gas measurement device in which the movable portion is in close contact with the filter and the gas sensor.
Figure 2:
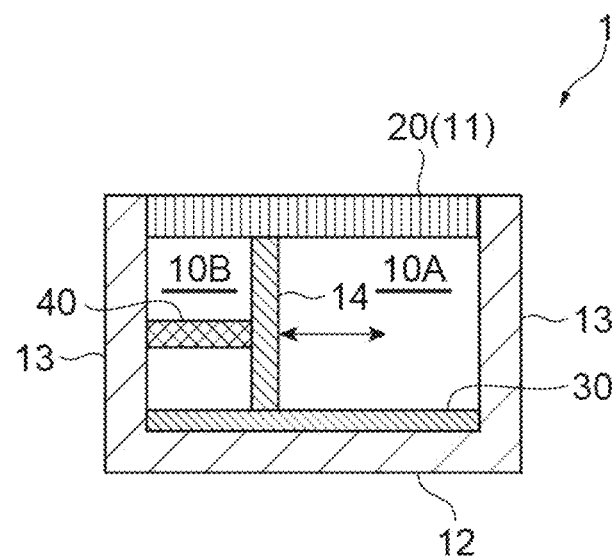

[First Embodiment] (A) of FIG. 2 is a cross-sectional view showing an example of the gas measurement device 1 including the movable portion 14 in the member 100 defining the gas chamber 10. In this configuration, the member 100 defining the gas chamber 10 includes an upper portion 11 including the filter 20, a bottom portion 12 on which the gas sensor 30 is disposed, and a side wall 13 and a movable portion 14 that are sandwiched between the upper portion 11 and the bottom portion 12. The upper portion 11 defines the top surface of the gas chamber 10, the bottom portion 12 defines the bottom surface of the gas chamber 10, and the side wall 13 and the movable portion 14 define the side surface of the gas chamber 10.

The MEMS actuator may be applied to the driving unit 40. The MEMS actuator has, for example, a comb-tooth structure that expands and contracts by an applied electrostatic force.

The movable portion 14 is at least the part of the member 100 that defines the gas chamber 10, and is moved by the driving unit 40. The movable portion 14 is connected to the upper portion 11, the bottom portion 12, and the side wall 13. As a more specific example, the movable portion 14 is airtightly connected to the upper portion 11, the bottom portion 12, and the side wall 13. The driving unit 40 moves the movable portion 14 in a direction approaching the filter 20 or a direction moving away from the filter 20. The movable portion 14 is moved along the upper portion 11, the bottom portion 12, and the side wall 13 by the driving unit 40.

When the movable portion 14 operates in a direction away from the filter 20, the volume of the gas chamber 10 increases. The pressure of the gas chamber 10 whose volume is increased is reduced, and external gas is supplied through the filter 20. When the movable portion 14 operates in a direction approaching the filter 20, the volume of the gas chamber 10 decreases. The pressure of the gas chamber 10 whose volume is reduced is increased, and the gas in the gas chamber 10 is exhausted through the filter 20.

(B) of FIG. 2 is a cross-sectional view showing an example of the gas measurement device 1 in which the movable portion 14 is in close contact with the filter 20 and the gas sensor 30. In this case, the gas chamber 10 includes a first gas chamber 10A and a second gas chamber 10B which are partitioned by the movable portion 14. In other words, the first gas chamber 10A and the second gas chamber 10B are defined by the upper portion 11, the bottom portion 12, the side wall 13, the movable portion 14, the filter 20, and the gas sensor 30. The movable portion 14 moves in accordance with expansion and contraction of the MEMS actuator in a state of being in close contact with each member defining the gas chamber 10.

When the MEMS actuators expand, the volumes of the first gas chambers 10A decrease and the volumes of the second gas chambers 10B increase. The reduced first gas chamber 10A is pressurized, and the gas in the first gas chamber 10A is discharged through the filter 20. The increased volume of the second gas chamber 10B is reduced, and external gas is supplied through the filter 20.

When the MEMS actuators contract, the volumes of the first gas chambers 10A increase and the volumes of the second gas chambers 10B decrease. The increased first gas chamber 10A is depressurized, and the external gas is supplied through the filter 20. The reduced second gas chamber 10B is pressurized, and the gas in the second gas chamber 10B is exhausted through the filter 20.

As described above, according to the gas measurement device 1 of the present embodiment, the movable portion 14 moves by the expansion and contraction of the driving unit 40. The volume of the gas chamber 10 defined by the movable portion 14 is increased or decreased by the movement of the movable portion 14. In this case, the gas measurement device 1 can suck gas by the expanding and contracting driving unit 40. The driving unit 40 may be made of a material and have a shape that allow gas to pass therethrough. In addition, when the movable portion 14 is in close contact with the filter 20 and the gas sensor 30, the gas measurement device 1 is downsized compared to the gas measurement device 1 in which the movable portion 14 is not in close contact with the filter 20 and the gas sensor 30.

Figure 3:
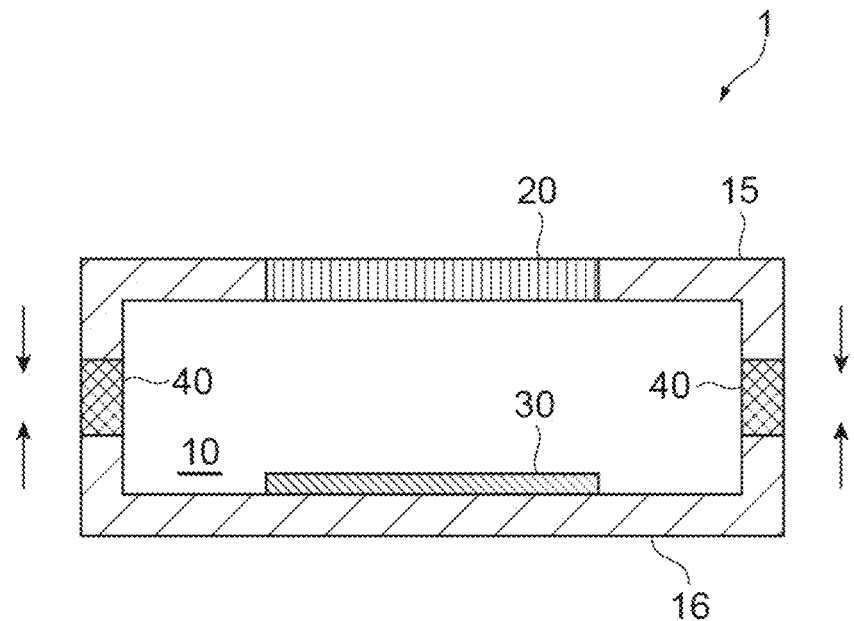
FIG. 3 (A) of is a cross-sectional view showing an example in which a gas measurement device including an upper container and a lower container in a member defining a gas chamber is contracted. (B) of FIG. 3 is a cross-sectional view showing an example in which a gas measurement device including an upper container and a lower container extends from a member defining a gas chamber.
Figure 3:
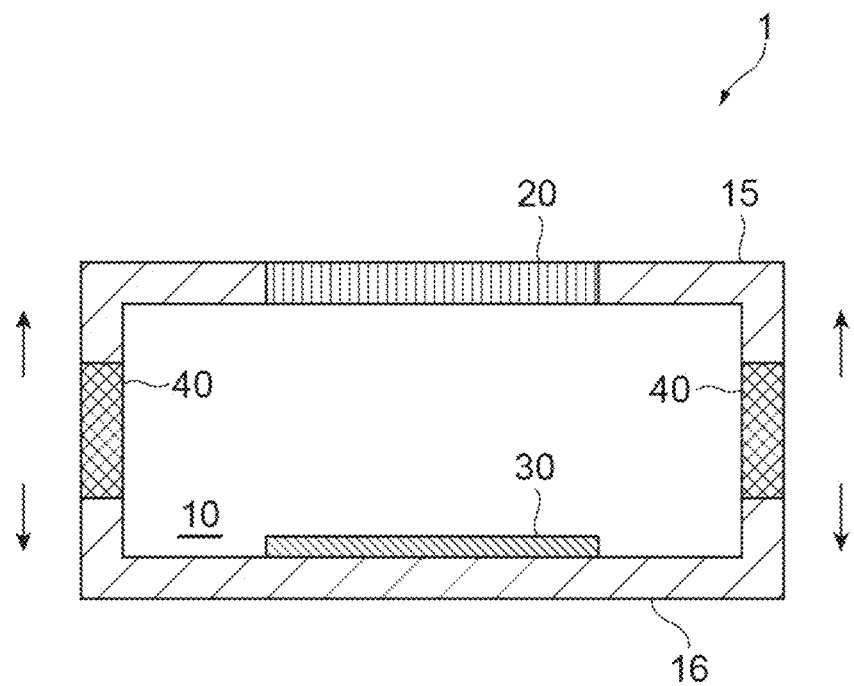

[Second Embodiment] (A) of FIG. 3 is a cross-sectional view showing an example in which the gas measurement device including the upper container 15 and the lower container 16 defining the gas chamber 10 is contracted. (B) of FIG. 3 is a cross-sectional view showing an example in which the gas measurement device including the upper container 15 and the lower container 16 is extended. In this configuration, the member 100 defining the gas chamber 10 includes the upper container 15 including the filter 20, the lower container 16 including the gas sensor 30, and the driving unit 40 sandwiched between the upper container 15 and the lower container 16. The upper container 15 has an opening at a lower end thereof, and the lower container 16 has an opening at an upper end thereof. The upper container 15 is at least the part of the member 100 that defines the gas chamber 10, and is moved in the up-down direction by the driving unit 40.

The piezoelectric actuator may be applied to the driving unit 40. The piezoelectric actuator includes, for example, laminated piezoelectric elements that expand and contract in accordance with an applied voltage.

The piezoelectric element is a passive element that deforms in accordance with an applied voltage. The piezoelectric actuator is held between an upper container 15 and a lower container 16 so as not to pass gas. The piezoelectric actuator alternately repeats a state in which it expands and relatively moves the upper container 15 upward and a state in which it contracts and relatively moves the upper container 15 downward.

When the piezoelectric actuator expands and moves the upper container 15 upward, the volume of the gas chamber 10 increases. The pressure of the gas chamber 10 whose volume is increased is reduced, and external gas is supplied through the filter 20. When the piezoelectric actuator contracts and moves the upper container 15 downward, the volume of the gas chamber 10 decreases. The pressure of the gas chamber 10 whose volume is reduced is increased, and the gas in the gas chamber 10 is exhausted through the filter 20.

As described above, according to the gas measurement device 1 of the present embodiment, the gas flow that has passed through the filter 20 is perpendicular to the gas sensor 30. In this case, the gas measurement device 1 can stabilize the sucked gas flow.

Figure 4:
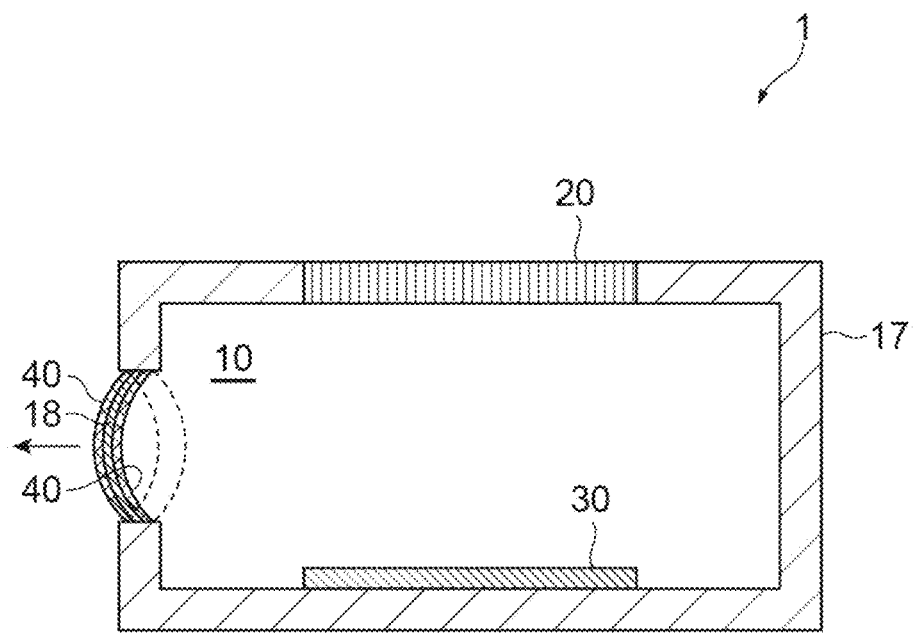
FIG. 4 is a cross-sectional view showing an example of a gas measurement device including an elastic member in a member defining a gas chamber.

[Third Embodiment] FIG. 4 is a cross-sectional view showing an example of the gas measurement device 1 including the elastic member 18 in the member 100 defining the gas chamber 10. In this configuration, the member 100 defining the gas chamber 10 includes a container 17 provided with an opening and in which the filter 20 and the gas sensor 30 are disposed, and a film-like elastic member fixed to the container so as to close the opening. The elastic member 18 is at least the part of the member 100 that defines the gas chamber 10, and is moved by the driving unit 40.

The driving unit 40 may be a piezoelectric element. The piezoelectric element is configured to sandwich the elastic member 18. The piezoelectric element elastically deforms the elastic member 18 so as to protrude in accordance with applied voltage. The elastic member 18 is moved integrally with the piezoelectric element by elastic deformation. This structure in which the elastic member 18 and the piezoelectric element sandwiching the elastic member 18 are integrated may be a piezo pump. The gas chamber 10 defined by the elastic member 18 alternately repeats a state of protruding to the inside and a state of protruding to the outside.

When the gas chamber 10 protrudes in a convex shape with respect to the inside, the volume of the gas chamber 10 decreases. The pressure of the gas chamber 10 whose volume is reduced is increased, and the gas in the gas chamber 10 is exhausted. When the gas chamber 10 protrudes outward, the volume of the gas chamber 10 increases. The pressure of the gas chamber 10 whose volume is increased is reduced, and external gas is supplied through the filter 20.

As described above, according to the gas measurement device 1 of the present embodiment, compared to the gas measurement device 1 in which the elastic member 18 is not included in at least a part of the member 100 defining the gas chamber 10, the gas measurement device 1 can intake gas with a simple structure.

[Fourth Embodiment]

The member 100 defining the gas chamber 10 may include a valve 50. The valve 50 is opened when the pressure of the gas chamber 10 is higher than the external pressure, and is closed when the pressure of the gas chamber 10 is lower than the external pressure. As an example, the valve 50 is formed of a substantially plate-shaped elastic member. The valve 50 is provided so as to separate the gas chamber 10 from the outside. One side of the substantially plate-shaped valve 50 is connected to a member 100 defining a gas chamber. On the other side, the valve 50 abuts the outer surface of the member 100 defining the gas chamber.

(A) of FIG. 5 is a cross-sectional view showing an example of the gas measurement device 1 in which the valve 50 is closed. In this configuration, the member 100 defining the gas chamber 10 includes the movable portion 14 and the valve 50. The movable portion 14 moves in a direction away from the filter 20. The volume of the gas chamber 10 increases and the pressure decreases. When the pressure in the gas chamber 10 is lower than the external pressure, an internal pressure is applied to the valve 50 from the outside. In this case, the valve 50 is blocked against the outer surface of the side wall 13. The external gas is supplied through the filter 20.

(B) of FIG. 5 b is a cross-sectional view showing an example of the gas measurement device 1 in which the valve 50 is opened. The movable portion 14 moves in a direction approaching the filter 20. The volume of the gas chamber 10 decreases and the pressure increases. When the pressure in the gas chamber 10 is higher than the external pressure, an external pressure is applied to the valve 50 from the inside. In this case, the valve 50 is elastically deformed to the outside of the side wall 13 and opened. The gas in the gas chamber 10 is mainly exhausted through the valve 50.

As described above, according to the gas measurement device 1 of the present embodiment, compared to the gas measurement device 1 in which the valve 50 is not included in the member that defines the gas chamber 10, the gas measurement device 1 can exhaust the gas in the gas chamber 10 at high speed.

[Modification] While various exemplary embodiments have been described above, various omissions, substitutions and changes may be made without being limited to the exemplary embodiments described above.

In the gas measurement device 1 shown in (A) of FIG. 2, (A) and (B) of FIG. 5, a vent hole (not shown) may be provided in the side wall 13. The vent hole is provided in the side wall 13 in which the driving unit 40 is provided. The vent hole communicates between the outside and the inside of the side wall 13. Gas in a space defined by a surface on which the driving unit 40 is provided and the movable portion 14 is sucked and discharged through the vent hole. In this case, since the pressure applied to the movable portion 14 is reduced, the gas measurement device 1 can reduce the force for moving the movable portion 14.

The gas sensor 30 may not be a semiconductor type sensor. For example, the gas sensor 30 may be an electrochemical sensor, a quartz crystal sensor, a surface acoustic wave sensor, or a combination thereof.

The driving unit 40 may change the speed at which at least a part of the member 100 defining the gas chamber 10 is moved. When the driving unit 40 moves at least the part of the member 100 at high speed, the gas measurement device 1 can improve the response speed for detecting gas. When the driving unit 40 moves at least the part of the member 100 at a low speed, the gas measurement device 1 can reduce current consumption of the driving unit 40.

The gas measurement device 1 including the valve 50 in the member 100 defining the gas chamber 10 may include an upper container 15 and a lower container 16. The gas measurement device 1 including the valve 50 in the member 100 defining the gas chamber 10 may include an elastic member 18. The valve 50 formed by a substantially plate-shaped rigid member may be connected by a hinge to the member 100 defining the gas chamber 10.

REFERENCE SIGNS LIST

* * * gas measurement device, 10 * * * gas chamber, 10A * * * first gas chamber, 10B * * * second gas chamber, 11 * * * upper portion, 12 * * * bottom portion, 13 * * * side wall, 14 * * * movable portion, 15 * * * upper container, 16 * * * lower container, 17 * * * container, 18 * * * elastic member, 20 * * * filter, 30 * * * gas sensor, 40 * * * driving unit, 50 * * * valve.

The invention claimed is:

1. A gas measurement device comprising:
a gas sensor disposed in a gas chamber;
a filter configured to control passing gas molecules to the gas chamber; and
a driving unit configured to move at least a part of a member defining the gas chamber,
wherein the member that defines the gas chamber includes:
an upper portion defining a top surface of the gas chamber and including the filter;
a bottom portion defining a bottom surface of the gas chamber and in which the gas sensor is disposed;
a side wall defining a side surface of the gas chamber and sandwiched between the upper portion and the bottom portion; and
a movable portion that defines a side surface of the gas chamber together with the side wall and is connected to the upper portion, the bottom portion, and the side wall, and
wherein the at least the part of a member that defines the gas chamber and is moved by the driving unit is the movable portion, and
wherein the driving unit moves the movable portion along the top surface, the bottom surface, and the side wall.

2. The gas measurement device according to claim 1, wherein the movable portion is in close contact with the gas sensor and the filter, and the driving unit moves the movable portion along the gas sensor and the filter.

3. The gas measurement device according to claim 1, wherein the member that defines the gas chamber includes a valve that is opened when a pressure of the gas chamber is higher than an external pressure and is closed when the pressure of the gas chamber is lower than the external pressure.

4. The gas measurement device according to claim 2, wherein the member that defines the gas chamber includes a valve that is opened when a pressure of the gas chamber is higher than an external pressure and is closed when the pressure of the gas chamber is lower than the external pressure.

5. The gas measurement device according to claim 1, wherein the driving unit moves the movable portion to vary volume of the gas chamber.

6. The gas measurement device according to claim 2, wherein the driving unit moves the movable portion to vary volume of the gas chamber.

7. The gas measurement device according to claim 3, wherein the driving unit moves the movable portion to vary volume of the gas chamber.

* * * * *